United States Patent
Cho et al.

(10) Patent No.: US 10,251,607 B2
(45) Date of Patent: Apr. 9, 2019

(54) METHOD AND APPARATUS FOR MEASURING BIO SIGNAL

(71) Applicant: SAMSUNG ELECTRONICS CO., LTD., Suwon-si (KR)

(72) Inventors: Jae-geol Cho, Yongin-si (KR); Kwang-choon Kim, Suwon-si (KR); Jae-pil Kim, Seongnam-si (KR); Jin-hong Min, Suwon-si (KR); Hyun-jae Baek, Seoul (KR); Hang-sik Shin, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/163,073

(22) Filed: May 24, 2016

(65) Prior Publication Data

US 2016/0262702 A1 Sep. 15, 2016

Related U.S. Application Data

(63) Continuation of application No. PCT/KR2014/001973, filed on Mar. 11, 2014.

(30) Foreign Application Priority Data

Nov. 25, 2013 (KR) .................. 10-2013-0143950

(51) Int. Cl.
*A61B 5/00* (2006.01)
*A61B 5/0402* (2006.01)
(Continued)

(52) U.S. Cl.
CPC .............. *A61B 5/6898* (2013.01); *A61B 5/01* (2013.01); *A61B 5/0402* (2013.01);
(Continued)

(58) Field of Classification Search
CPC ..... A61B 5/01; A61B 5/0402; A61B 5/04085; A61B 5/053; A61B 5/14551;
(Continued)

(56) References Cited

U.S. PATENT DOCUMENTS

| 8,332,019 B2 | 12/2012 | Shimuta et al. |
| 2010/0324388 A1* | 12/2010 | Moon .................... A61B 5/746 600/324 |

(Continued)

FOREIGN PATENT DOCUMENTS

| CN | 102368949 A | 3/2012 |
| EP | 2415397 B1 | 6/2015 |

(Continued)

OTHER PUBLICATIONS

International Search Report dated Aug. 22, 2014, by the International Searching Authority in counterpart International Patent Application No. PCT/KR2014/001973 (PCT/ISA/210).

(Continued)

*Primary Examiner* — Tony O Davis
(74) *Attorney, Agent, or Firm* — Sughrue Mion, PLLC (57) ABSTRACT

A physiological signal measurement apparatus includes a battery cover covering an area where a battery of a terminal device is detachably attached, a sensor unit detecting a physiological signal, the sensor unit being included in the battery cover, and a control unit controlling the sensor unit to detect the physiological signal, wherein the physiological signal measurement apparatus is detachably attached to the terminal device as the battery cover is detachably attached to the terminal device.

14 Claims, 7 Drawing Sheets

(51) Int. Cl.
    *A61B 5/053*     (2006.01)
    *A61B 5/1455*     (2006.01)
    *A61B 5/01*     (2006.01)
    *A61B 5/0408*     (2006.01)
    *G06F 19/00*     (2018.01)

(52) U.S. Cl.
    CPC .......... *A61B 5/04085* (2013.01); *A61B 5/053* (2013.01); *A61B 5/14551* (2013.01); *A61B 5/4872* (2013.01); *A61B 5/7275* (2013.01); *A61B 5/7435* (2013.01); *G06F 19/00* (2013.01)

(58) Field of Classification Search
    CPC ... A61B 5/4872; A61B 5/6898; A61B 5/7275; A61B 5/7435
    USPC .......................... 600/301; 345/156, 170–176
    See application file for complete search history.

(56) References Cited

U.S. PATENT DOCUMENTS

| | | | |
|---|---|---|---|
| 2011/0015496 A1* | 1/2011 | Sherman | A61B 5/0006 600/301 |
| 2011/0301435 A1 | 12/2011 | Albert et al. | |
| 2012/0022385 A1 | 1/2012 | Shimuta et al. | |
| 2012/0238832 A1* | 9/2012 | Jang | A61B 5/0205 600/301 |
| 2012/0238834 A1* | 9/2012 | Hornick | A61B 5/02416 600/301 |
| 2013/0274565 A1* | 10/2013 | Langer | A61N 1/3993 600/301 |
| 2013/0278552 A1* | 10/2013 | Kamin-Lyndgaard | G09G 5/006 345/174 |
| 2013/0310656 A1 | 11/2013 | Lim et al. | |
| 2013/0324868 A1* | 12/2013 | Kaib | A61N 1/3937 600/510 |
| 2013/0331719 A1* | 12/2013 | Freeman | A61B 5/046 600/518 |
| 2013/0338460 A1* | 12/2013 | He | A61B 5/0205 600/324 |
| 2014/0143155 A1* | 5/2014 | Karlov | G04G 99/006 705/71 |
| 2014/0269224 A1* | 9/2014 | Huh | G04G 13/021 368/73 |
| 2014/0278139 A1* | 9/2014 | Hong | A61B 5/4866 702/19 |
| 2015/0324564 A1* | 11/2015 | Sahu | G06F 21/45 726/19 |
| 2017/0171727 A1* | 6/2017 | DeLoy | H04W 4/16 |

FOREIGN PATENT DOCUMENTS

| | | |
|---|---|---|
| JP | 2011-217861 A | 11/2004 |
| KR | 10-2005-0011283 A | 1/2005 |
| KR | 10-2005-0105822 A | 11/2005 |
| KR | 10-2006-0133607 A | 12/2006 |
| KR | 10-1030887 B1 | 4/2011 |
| KR | 10-2012-0097219 A | 9/2012 |
| KR | 10-1246726 B1 | 3/2013 |
| WO | 2013/155196 A2 | 10/2013 |

OTHER PUBLICATIONS

Written Opinion dated Aug. 22, 2014, by the International Searching Authority in counterpart International Patent Application No. PCT/KR2014/001973 (PCT/ISA/237).

Communication dated Jul. 12, 2017, issued by the European Patent Office in counterpart European Application No. 14864547.6.

Communication dated Jul. 4, 2018, from the State Intellectual Property Office of People's Republic of China in counterpart Chinese Application No. 201480064389.4.

* cited by examiner

METHOD AND APPARATUS FOR MEASURING BIO SIGNAL

CROSS REFERENCE TO RELATED APPLICATIONS

This application is a continuation of International Application No. PCT/KR2014/001973 filed on Mar. 11, 2014, which claims priority from Korean Patent Application No. 10-2013-0143950 filed on Nov. 25, 2013, the contents of which are incorporated herein by reference in their entirety.

TECHNICAL FIELD

The present invention relates to an apparatus and method for measuring a physiological signal, and more particularly, to an apparatus and method for measuring a physiological signal in a mobile device.

BACKGROUND ART

As interests in health issues have rapidly increased along with an increase in the incidence rates of various diseases, the demand for and distribution of apparatuses for personally checking different health problems, for example, a blood glucose meter or a blood pressure meter, have increased too. In particular, a body state of a patient suffering from a disease, such as, diabetes or blood pressure, is checked as occasion demands and monitored continuously. Accordingly, a compact measurement apparatus capable of checking a health state of a patient as occasion demands, without the need for the patient to visit a hospital, has been researched and developed. In particular, a mobile healthcare system using an application program for a mobile phone, for example, a smartphone, has been researched and developed.

In a mobile healthcare system, a user may check his/her health state by interoperating a mobile phone, for example, a smartphone, with a separate portable measurement apparatus. In other words, in order to use an existing mobile healthcare system, a user carries a measurement apparatus apart from a mobile phone. Thus, it is inconvenient to carry such an apparatus, and further, it is difficult to carry out a variety of tests.

DETAILED DESCRIPTION OF THE INVENTION

Technical Solution

The present invention provides an apparatus and method for measuring a physiological signal, the apparatus being mounted in a battery cover of a mobile device.

Advantageous Effects

According to one or more of embodiments of the present invention, an apparatus for measuring a physiological signal is included in a battery cover of a mobile terminal so that the size or thickness of the mobile device may not be increased.

According to an embodiment of the present invention, a physiological signal may be measured by using power of a mobile terminal.

BEST MODE

According to an aspect of the present invention, there is provided a physiological signal measurement apparatus includes a battery cover covering an area where a battery of a terminal device is detachably attached, a sensor unit detecting a physiological signal, the sensor unit being included in the battery cover, and a control unit controlling the sensor unit to detect the physiological signal, wherein the physiological signal measurement apparatus is detachably attached to the terminal device as the battery cover is detachably attached to the terminal device.

The physiological signal measurement apparatus may further include a power unit that is connected to the terminal device to receive power from the terminal device.

The battery cover may further include a flip cover that covers a display of the terminal device and the sensor unit is included in the flip cover.

The physiological signal measurement apparatus may further include a communication unit that receives a message requesting detection of the physiological signal and transmits information about the physiological signal detected by the sensor unit according to the received message to an external device or the terminal device, wherein the control unit controls the sensor unit and the communication unit according to the received message.

According to an aspect of the present invention, there is provided a terminal device including a physiological signal measurement unit comprising a battery cover covering an area where a battery of the terminal device is detachably attached and a sensor detecting a physiological signal, the sensor being included in the battery cover, a communication unit transceiving data with the physiological signal measurement unit, a control unit controlling a display to display information about a detected physiological signal, and the display displaying the information about the detected physiological signal, wherein the physiological signal measurement unit is detachably attached to the terminal device as the battery cover is detachably attached to the terminal device.

The terminal device may further include a power unit that supplies power to the terminal device, wherein the power unit is connected to the physiological signal measurement unit to supply power to the physiological signal measurement unit.

The battery cover may further include a flip cover that covers the display of the terminal device and the sensor unit is included in the flip cover.

The physiological signal measurement unit may generate physiological contact state information including an area where a physiological contact is detected as a sensor measuring a physiological signal detects the physiological contact, the communication unit may receive the generated physiological contact state information, and the display may display the received physiological contact state information.

The control unit or the physiological signal measurement unit determines whether the physiological signal is measurable based on the physiological contact state information, the terminal device further comprises an output unit that outputs a result of the determination via a sound signal or a vibration signal, and the output unit or the display outputs the result of the determination.

The display may be a touch screen that detects an input in a predetermined area of the display, and as the touch screen detects a physiological contact in the predetermined area of the display, the control unit may control the physiological signal measurement unit to detect the physiological contact.

As the touch screen detects the input in the predetermined area of the display and the sensor of the physiological signal measurement unit detects the physiological contact, the control unit may control the physiological signal measurement unit to initiate measurement of a physiological signal.

As the sensor of the physiological signal measurement unit detects the physiological contact and the touch screen detects the input in the predetermined area of the display, the control unit may control the physiological signal measurement unit to initiate measurement of a physiological signal.

When the physiological signal is measurable, the physiological signal measurement unit may measure a physiological signal and transmits a result of the measurement to the control unit.

According to an aspect of the present invention, there is provided a method of measuring a physiological signal at a terminal device, which includes detecting a physiological contact by using a physiological signal measurement unit that measures the physiological signal, generating physiological contact state information about an area where the physiological contact is detected, and displaying the generated physiological contact state information on a display.

The physiological signal measurement unit may be included in a battery cover that is disposed in an area where a battery of the terminal device is detachably attached.

The method may further include determining whether the physiological signal is measurable, based on the physiological contact state information, and outputting a result of the determination.

The detection of the physiological contact may include detecting an input in a predetermined area of the display, and detecting a physiological contact by using the physiological signal measurement unit that measures the physiological signal, according to a result of the detection of the input.

The method may further include starting the measurement of a physiological signal by sequentially detecting the input in the predetermined area of the display and the physiological contact by using a sensor.

The method may further include starting the measurement of a physiological signal by sequentially detecting the physiological contact by using a sensor and the input in the predetermined area of the display.

The method may further include, when the physiological signal is measurable, measuring the physiological signal and displaying a result of the measurement.

According to an aspect of the present invention, there is provided a method of measuring a physiological signal at a physiological signal measurement apparatus, which includes detecting a physiological contact, generating physiological contact state information about an area where the physiological contact is detected, and transmitting the generated physiological contact state information to a terminal device or an external device.

The physiological signal measurement apparatus may be included in a battery cover disposed in an area where a battery of the terminal device is detachably attached.

The method may further include, when the physiological signal is measurable, measuring the physiological signal and transmitting a result of the measurement to the terminal device or the external device.

MODE OF THE INVENTION

The present invention will now be described more fully with reference to the accompanying drawings, in which embodiments of the invention are shown. In the following description, when detailed descriptions about related well-known functions or structures are determined to make the gist of the present invention unclear, the detailed descriptions will be omitted herein. Throughout the drawings, like reference numerals denote like elements.

The terms used in the present invention have been selected from currently widely used general terms in consideration of the functions in the present invention. However, the terms may vary according to the intention of one of ordinary skill in the art, case precedents, and the advent of new technologies. Also, for special cases, meanings of the terms selected by the applicant are described in detail in the description section. Accordingly, the terms used in the present invention are defined based on their meanings in relation to the contents discussed throughout the specification, not by their simple meanings.

When a part may "include" a certain constituent element, unless specified otherwise, it may not be construed to exclude another constituent element but may be construed to further include other constituent elements. Terms such as " . . . unit", "~module", etc. stated in the specification may signify a unit to process at least one function or operation and the unit may be embodied by hardware, software, or a combination of hardware and software.

Embodiments are provided to further completely explain the present invention to one of ordinary skill in the art to which the present invention pertains. However, the present invention is not limited thereto and it will be understood that various changes in form and details may be made therein without departing from the spirit and scope of the following claims. In the drawings, a part that is not related to a description is omitted to clearly describe the present invention and, throughout the specification, similar parts are referenced with similar reference numerals.

In the present specification, although the apparatus and method according to an embodiment of the present invention are described to measure a physiological signal of a "human body", the present invention is not limited thereto and may be applied to the measurement of a physiological signal of a "living thing".

Hereinafter, the present invention will be described in detail by explaining embodiments of the invention with reference to the attached drawings.

Figure 1:
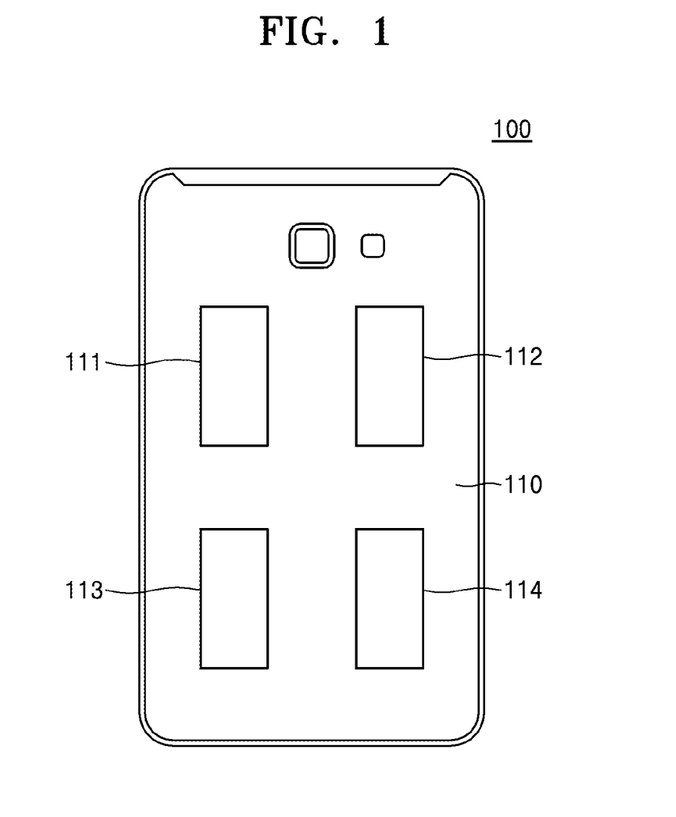
FIG. 1 illustrates an example of a physiological signal measurement apparatus according to an embodiment of the present invention.

FIG. 1 illustrates an example of a physiological signal measurement apparatus 110 according to an embodiment of the present invention.

Referring to FIG. 1, the physiological signal measurement apparatus 110 according to the present embodiment may include a battery cover of a terminal device 100 and constituent elements to measure a physiological signal, for example, one or more conductive electrodes 111, 112, 113, and 114 that are illustrated in FIG. 1.

Instead of the battery cover of the terminal device 100, the physiological signal measurement apparatus 110 may be detachably attached to the terminal device 100 via the battery cover of the physiological signal measurement apparatus 110 that is detachably attached to the terminal device 100. Accordingly, without increasing the thickness or size of the terminal device 100, the physiological signal measurement apparatus 110 may be detachably attached to the terminal device 100. Also, as the physiological signal measurement apparatus 110 may receive power from a battery (not shown) of the terminal device 100 placed in from the battery cover.

The one or more conductive electrodes 111, 112, 113, and 114 measure a physiological signal and are provided on the battery cover of the terminal device 100.

A physiological signal is an electrical signal that may be generated by electrochemically changing a resistance of nerve cells and muscle cells.

A plurality of conductive electrodes 111, 112, 113, and 114 may detect an electrical signal that is measured from a human body when there is a physiological contact. As a sensed signal is processed, a physiological signal may be measured.

In addition, the conductive electrodes 111, 112, 113, and 114 may measure a value of body fat of a living thing. The conductive electrodes 111, 112, 113, and 114 may measure at least one physiological signal by transmitting an electronic current to the living thing and measuring an amount of a change in a resistance in the living thing.

The physiological signal measurement apparatus 110 is not limited thereto and may further include other constituent elements to measure a physiological signal, for example, an optical sensor or an inertial sensor. The constituent element to measure a physiological signal is described in detail with reference to FIGS. 2 and 3.

Figure 2:
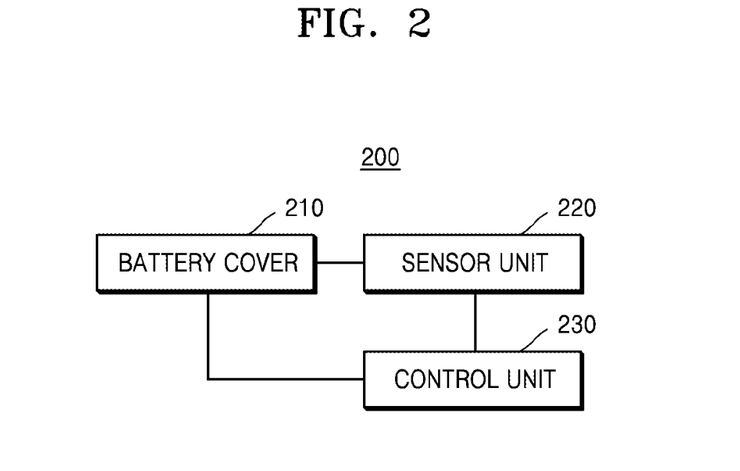
FIGS. 2 and 3 are block diagrams of an internal structure of a physiological signal measurement apparatus according to an embodiment of the present invention.
Figure 3:
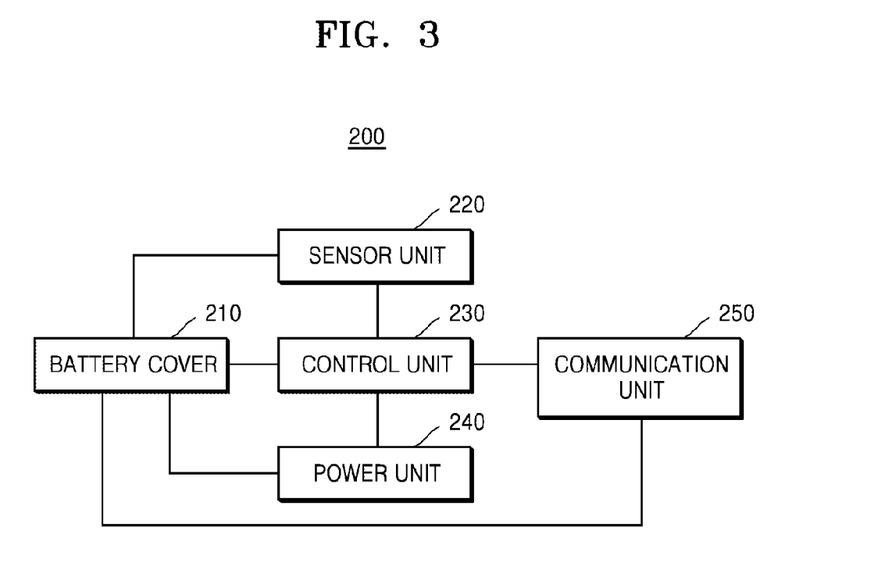

FIGS. 2 and 3 are block diagrams of an internal structure of a physiological signal measurement apparatus 200 according to an embodiment of the present invention.

Referring to FIG. 2, the physiological signal measurement apparatus 200 according to the present embodiment may include a battery cover 210, a sensor unit 220, and a control unit 230. However, not all of the illustrated constituent elements are essential constituent elements. The physiological signal measurement apparatus 200 may be embodied by using a larger number of constituent elements than the number of the illustrated constituent elements or by using a smaller number of constituent elements than the number of the illustrated constituent elements.

The above-described constituent elements are described below.

The battery cover 210 covers an area for attachment and detachment of the battery of the terminal device 100. The sensor unit 220 and the control unit 230 of the physiological signal measurement apparatus 200 may be provided on the battery cover 210.

In the present embodiment, the sensor unit 220 to measure a physiological signal may be provided on a rear surface of the battery cover 210. The control unit 230 to process the physiological signal may be provided on a front surface of the battery cover 210 or within the battery cover 210. Accordingly, when a user contacts the sensor unit 220 that is arranged at the rear surface of the battery cover 210, the sensor unit 220 may measure a user's physiological signal.

The sensor unit 220 may include at least one sensor to measure the physiological signal. The sensor unit 220 according to the present embodiment may include at least one of the conductive electrode, a temperature sensor, and an optical sensor.

The conductive electrode may measure at least one value of an electrocardiogram (ECG) and body fat of a living thing. The conductive electrode may be formed of a material having conductive properties in order to measure body fat based on an amount of a change in a resistance in a human body or an ECG signal having electrical properties and occurring with heart beats of the human body.

An ECG is used to record the electrical activity of the heart in time by using electrodes attached to skin. An ECG value may be measured by observing and amplifying a change in a tiny electrical signal occurring due to depolarization whenever muscles of the heart contract.

In the present embodiment, four or more conductive electrodes may be provided in the sensor unit 220. In the physiological signal measurement apparatus 110, when an ECG value is measured by using four (4) or more conductive electrodes, noise may be removed through a driven-right-leg (DRL) so that an accurate value may be obtained compared to a method of measuring an ECG value by using two (2) conductive electrodes.

An electrical signal that is measured from a human body may have a tiny voltage of several microvolts ($\mu V$). Thus, a measured ECG value may not be accurate due to interference with a physiological signal. The physiological signal measurement apparatus 200 may remove noise mixed with the physiological signal that is an electrical signal measured from the human body by using physiological signals that are measured from different parts of the human body by using the DRL.

The ECG value may be measured by using two or more electrodes of the four electrodes. The ECG value may be measure by using three (3) electrodes. However, when one electrode is not able to measure a physiological signal due to a skin contact defect, the ECG value may be measured by using two (2) electrodes.

A body fat amount may be measured by measuring a bioelectrical impedance considering that, when a tiny AC signal is transmitted to a human body, different impedances are generated from body fat, muscle, moisture, etc. The body fat amount may be measured by using at least four (4) conductive electrodes.

A temperature sensor may measure a bio temperature. The temperature sensor may include a temperature sensor such as a thermistor, a thermocouple, radiation, and IC, or other type of a temperature sensor.

An optical sensor may measure a pulse wave or oxygen saturation of a human body. The optical sensor may measure a pulse wave or oxygen saturation by scanning light from a light source into the human body through skin and detecting a transmitting light at a light receiving unit. Accordingly, the optical sensor to measure a physiological signal may include a light emitting sensor for generating light and a light receiving sensor for absorbing light from the human body. The optical sensor may include a light emitting sensor having at least one wavelength and a light receiving sensor and detect a physiological signal such as a pulse wave or oxygen saturation.

In the present embodiment, the conductive electrode as illustrated in FIG. 1 may be arranged at the rear surface of the battery cover 210 so that each hand of the user may contact two conductive electrodes. However, the present embodiment is not limited thereto and the conductive electrode may be arranged at a side surface of the battery cover 210. For example, two conductive electrodes may be arranged at each of opposite side surfaces of the battery cover 210. The optical sensor may be arranged on the conductive electrode, but the present invention is not limited thereto and the optical sensor may be arranged at a different position.

Also, the sensor unit 220 may further include an inertial sensor to remove noise that may occur due to shaking of the physiological signal measurement apparatus 200.

The inertial sensor may include an acceleration sensor and a gyro sensor. The gyro sensor may measure acceleration that occurs by a movement of the physiological signal measurement apparatus 200. Also, the gyro sensor may measure an angular velocity from the movement of the physiological signal measurement apparatus 200.

The physiological signal measurement apparatus 200 according to the present embodiment may use the inertial sensor that may detect shaking of the physiological signal measurement apparatus 200 to remove an error that may occur due to the shaking of the physiological signal measurement apparatus 200. In other words, the physiological signal measurement apparatus 200 may detect the shaking of the physiological signal measurement apparatus 200 by using the inertial sensor. The physiological signal measured during the above detection may be analyzed by allowing the physiological signal to pass through a filter for removing noise or by excluding a physiological signal that is measured during the shaking. Accordingly, an error in a measured value that is generated due to the shaking of the physiological signal measurement apparatus 200 may be removed.

The control unit 230 may typically control the overall operation of the physiological signal measurement apparatus 200. For example, the control unit 230 may control the physiological signal measurement apparatus 200 to measure a physiological signal according to the detection of physiological contact. The control unit 230 may be provided on an inner surface of the battery cover 210 or on an inner or outer surface of an inner cover of the battery cover 210. The inner cover may be provided on the inner surface of the battery cover 210 and may be separated from the battery cover 210.

Also, the control unit 230 may control the physiological signal measurement apparatus 200 to convert a measured physiological signal to an electrical signal and transmit a converted signal to the terminal device 100 or an external device. However, the present embodiment is not limited thereto and the control unit 230 may control the physiological signal measurement apparatus 200 to process and analyze the measured physiological signal and transmit data including a result of the analysis to the terminal device or the external device. For example, the control unit 230 may control the physiological signal measurement apparatus 200 to analyze a measured ECG signal and determine whether the measured ECG signal is normal and transmit data including a result of the determination to the terminal device or the external device.

In addition, the control unit 230 may filter the physiological signal measured by the sensor unit 220 or analyze the physiological signal by using a variety of methods, such as, detection of ECG beats, detection of pulse waves, calculation of number of heart beats, detection of irregular pulses, calculation of a pulse wave arrival time, extraction of a blood vessel health level, calculation of oxygen saturation, and calculation of a body fat rate. The analysis of the measured physiological signal may be performed not only by the physiological signal measurement apparatus 200 but also by the terminal device 400 that receives the measured physiological signal.

Referring to FIG. 3, the physiological signal measurement apparatus 200 according to the present embodiment may include the battery cover 210, the sensor unit 220, the control unit 230, a power unit 240, and a communication unit 250. The battery cover 210, the sensor unit 220, and the control unit 230 of FIG. 3 respectively correspond to the battery cover 210, the sensor unit 220, and the control unit 230 of FIG. 2, and thus, redundant descriptions thereof are omitted. However, not all of the illustrated constituent elements are essential constituent elements. The physiological signal measurement apparatus 200 may be embodied by using a larger number of constituent elements than the number of the illustrated constituent elements or by using a smaller number of constituent elements than the number of the illustrated constituent elements.

The above-described constituent elements are described below.

The power unit 240 may supply power for measurement of a physiological signal to the physiological signal measurement apparatus 200. The power unit 240 may include a battery for supplying power or a connection portion such as a contact point to receive the power from the terminal device 100.

Since the physiological signal measurement apparatus 200 according to the present embodiment is provided on the battery cover 210, the physiological signal measurement apparatus 200 may easily access the terminal device 100 to receive power therefrom. Accordingly, the physiological signal measurement apparatus 200 may receive the power through the contact point to access the power of the terminal device 100. Accordingly, the physiological signal measurement apparatus 200 may not include a battery in the physiological signal measurement apparatus 200 or a wired or wireless device to receive power from an external source.

The communication unit 250 may include one or more constituent elements for performing communication between the physiological signal measurement apparatus 200 and the terminal device 100 or the external device. For example, the communication unit 160 may include a mobile communication module, a wireless internet module, a wired internet module, or a short-range communication module. The communication unit 160 may transceive data with the terminal device 100 or the external device by using at least one of the mobile communication module, the wireless internet module, the wired internet module, and the short-range communication module.

The mobile communication module may transceive wireless signals with at least one of a base station, an external terminal, and a server on a mobile communication network. The wireless signal may include a variety of types of data according to transceiving of voice call signals, video call signals, or a text/multimedia message.

The wireless internet module is a module for wireless Internet connection and may be internally or externally provided. Also, the wired Internet module is a module for wired Internet connection.

The short-range communication module is a module for short-range communication. Short-range communication technology may include Bluetooth, radio frequency identification (RFID), infrared data association (IrDA), ultra wideband (UWB), ZigBee, Wi-Fi Direct (WFD), or near field communication (NFC).

The communication unit 250 according to the present embodiment may receive a physiological signal measurement request from the external device or the terminal device 100 and transmit a measured physiological signal upon a received request to the external device or the terminal device 100. The communication unit 250 may transmit data including a result of analyzing a physiological signal or an electrical signal that is converted from the physiological signal by the control unit 230 to the external device or the terminal device 100.

The power unit 240 and the communication unit 250 may be provided with the control unit 230 on the inner cover or the inner surface of the battery cover 210.

The terminal device 100, to which the battery cover 210 is attached, is described in detail with reference to FIGS. 4 and 5.

The terminal device 400 may include a variety of types of apparatuses that are used by a user. For example, the terminal device 400 may include personal computers (PCs), notebook computers, mobile phones, tablet PCs, navigation terminals, smartphones, smart watches, personal digital assistants (PDAs), portable multimedia players (PMPs), and digital broadcast receivers. The above items are merely examples of the terminal devices 400. In addition to the above-mentioned items, any communication apparatuses, which are being developed and commercialized or may be developed in the future, may be included in the technical concept of the prevent invention.

Figure 4:
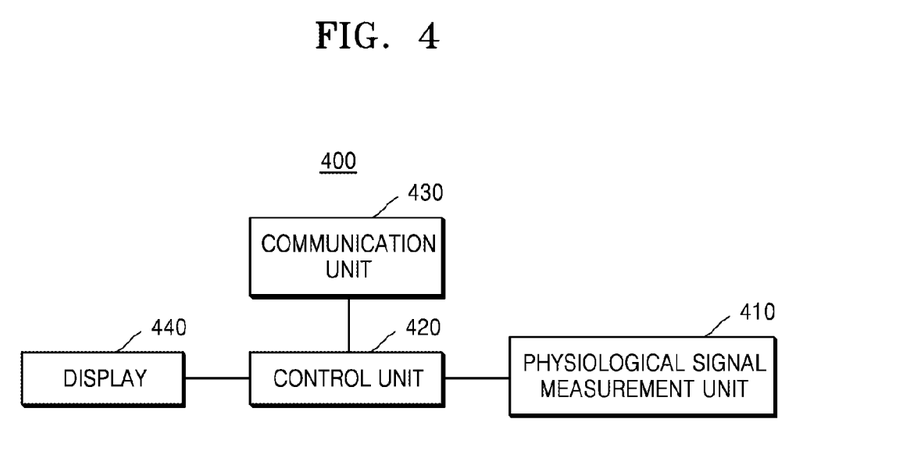
FIGS. 4 and 5 are block diagrams of an internal structure of a terminal device for measuring a physiological signal according to an embodiment of the present invention.
Figure 5:
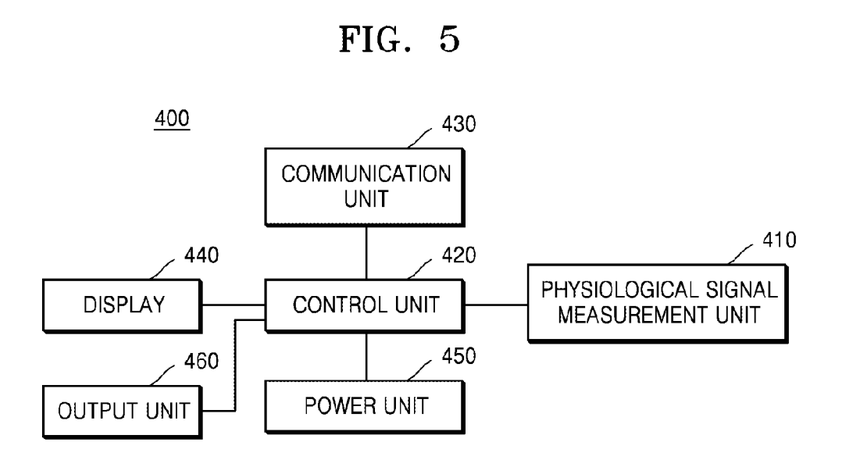

FIGS. 4 and 5 are block diagrams of an internal structure of a terminal device 400 for measuring a physiological signal according to an embodiment of the present invention.

Referring to FIG. 4, the terminal device 400 according to the present embodiment may include a physiological signal measurement unit 410, a control unit 420, a communication unit 430, and a display 440. However, not all of the illustrated constituent elements are essential constituent elements. Thus, the terminal device 400 may be embodied by using a larger number of constituent elements than the number of the illustrated constituent elements or by using a smaller number of constituent elements than the number of the illustrated constituent elements.

The above-described constituent elements are described below.

The physiological signal measurement unit 410 may correspond to the physiological signal measurement apparatus 200 of FIGS. 2 and 3. As described above, the physiological signal measurement unit 410 may be provided on the terminal device 400 as the battery cover of the physiological signal measurement unit 410 is attached on the terminal device 100. The physiological signal measurement unit 410 may measure a physiological signal upon a request of the terminal device 400 and transmit a measured physiological signal or data including a result of the analysis of the physiological signal to the terminal device 400.

The control unit 420 may typically control the overall operation of the terminal device 400. For example, the control unit 420 may control the terminal device 400 to request the physiological signal measurement unit 410 to perform measurement of a physiological signal according to a received input, receive the physiological signal, analyze a received physiological signal, and display a result of the analysis. Alternatively, the control unit 420 may control the terminal device 400 to receive and display the physiological signal or the data including the analysis result of the physiological signal.

In addition, the control unit 420 may filter the physiological signal that is measured by the physiological signal measurement unit 410 or analyze the physiological signal in a variety of methods, such as, detection of ECG beats, detection of pulse waves, calculation of number of heart beats, detection of irregular pulses, calculation of a pulse wave arrival time, extraction of a blood vessel health level, calculation of oxygen saturation, and calculation of a body fat rate.

Also, the control unit 420 may receive the physiological signal that is measured not only by the physiological signal measurement unit 410 but also by an external device capable of measuring the physiological signal, and analyze the received physiological signal. Alternatively, the control unit 420 may control such that data about the analyzed physiological signal from the external device is received and displayed.

The communication unit 430 may include one or more constituent elements for communicating between the terminal device 400 and the external device or the physiological signal measurement unit 410. For example, the communication unit 430 may include a mobile communication module, a wireless internet module, a wired internet module, or a short-range communication module. The communication unit 430 may transceive data with the external device or the physiological signal measurement unit 410 by using at least one of the mobile communication module, the wireless internet module, the wired internet module, and the short-range communication module.

In the present embodiment, the communication unit 430 may transmit a physiological signal measurement request to the external device or the physiological signal measurement unit 410 under the control of the control unit 420 and receive from the external device or the physiological signal measurement unit 410 the physiological signal or data including a result of the analysis of the physiological signal in response to the request.

The display 440 may display information that is processed by the terminal device 400. For example, the display 440 may measure the physiological signal and display a user interface (UI) or a graphical user interface (GUI) to display a result of the measurement. The display 440 may include at least one of a liquid crystal display, a thin film transistor-liquid crystal display, an organic light-emitting diode, a flexible display, and a 3D display. Two or more displays 440 may be used according an embodiment type of the terminal device 400.

The display 440 may form a mutual layer structure with a touch pad to receive a user input, thereby forming a touch screen. When the display 440 and the touch pad are configured to have a mutual structure forming a touch screen, the display 440 may be also used as an input device in addition to an output device.

In the present embodiment, as the display 440 that is configured to be a touch screen detects a user's touch input in a predetermined area, the measurement of a physiological signal may be automatically started. Also, the terminal device 400 may control the physiological signal measurement unit 410 so as to measure the physiological signal only when the user's touch input is detected in the predetermined area of the display 440.

Referring to FIG. 5, the terminal device 400 according to the present embodiment may includes the physiological signal measurement unit 410, the control unit 420, the communication unit 430, the display 440, a power unit 450, and an output unit 460. However, not all the illustrated constituent elements are essential constituent elements. The terminal device 400 may be embodied by using a larger number of constituent elements than the number of the illustrated constituent elements or by using a smaller number of constituent elements than the number of the illustrated constituent elements. The physiological signal measurement unit 410, the control unit 420, the communication unit 430, and the display 440 of FIG. 4 may respectively correspond to the physiological signal measurement unit 410, the control unit 420, the communication unit 430, and the display 440 of FIG. 5. Thus, redundant descriptions thereof area omitted.

The above-described constituent elements are described below.

The power unit 450 may include a power source for driving the terminal device 400 and supply power to the terminal device 400. The power unit 450 may supply the power to the terminal device 400 by including an element, such as a battery, for storing power or by being connected to an external power source in a wired or wireless manner.

The power unit 450 according to the present embodiment may be connected to the physiological signal measurement unit 410 and supply power to the physiological signal measurement unit 410. Accordingly, the physiological signal measurement unit 410 may be driven by receiving the power from the terminal device 400 without having to include a battery or be connected to the external source to receive power in a wired or wireless manner.

The output unit 460 may output information processed by the terminal device 400 by vibration or sound. For example, when the physiological signal is in a measurable state, the output unit 460 may output vibration or sound so as to inform a user of whether the physiological signal is in a measurable state. Also, when the physiological signal is changed from a measurable state to a non-measurable state, the output unit 460 may output a vibration signal or sound signal so as to inform the user that the physiological signal is in a non-measurable state. Also, when the physiological signal is being measured, the output unit 460 may output a vibration signal or sound signal to inform the user of the above state.

In addition to the above embodiment, when a preset event is generated, the output unit 460 may output a vibration signal or sound signal so as to output information about the measurement of the physiological signal.

Figure 6:
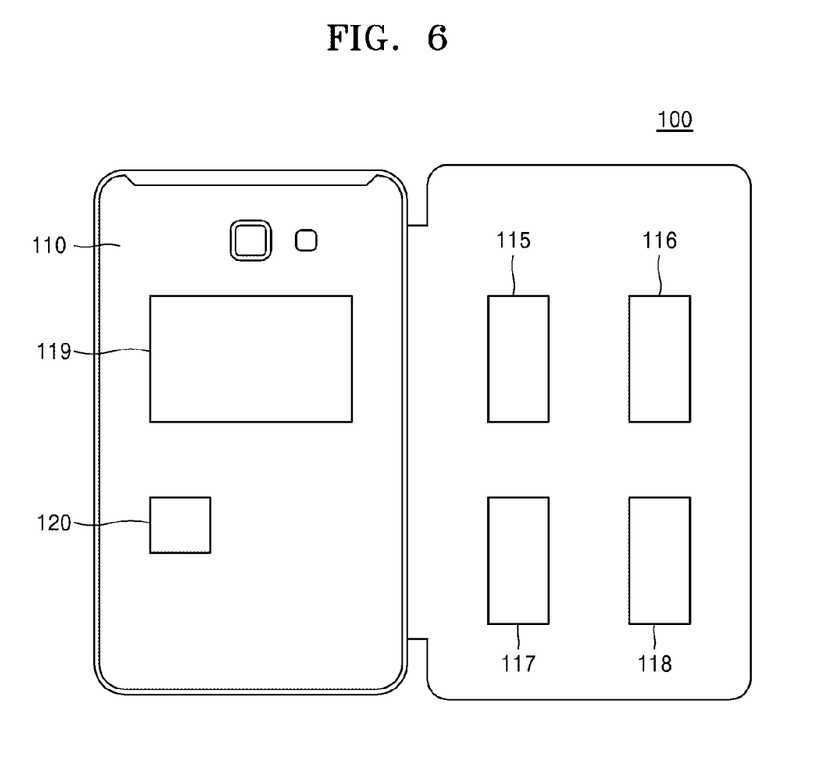
FIG. 6 illustrates an example of a physiological signal measurement apparatus having a flip cover according to an embodiment of the present invention.

FIG. 6 illustrates an example of a physiological signal measurement apparatus 110 having a flip cover according to an exemplary embodiment.

Referring to FIG. 6, the physiological signal measurement apparatus 110 includes a flip cover and may also include conductive electrodes 115 to 118 for measuring a physiological signal. The conductive electrodes 115 to 118 are provided on the flip cover. A control circuit 119 for controlling the physiological signal measurement apparatus 110, a contact point 120 through which power may be supplied to the physiological signal measurement apparatus 110, and a communication module (not shown) may be provided on a battery cover of the physiological signal measurement apparatus 110. The communication module may transmit the physiological signal or data including a result of analysis of the physiological signal to the terminal device 100 or an external device (not shown).

The flip cover is connected to the battery cover. Like the physiological signal measurement apparatus 100, as the battery cover is detachably attached to the terminal device 100, the flip cover may be detachably attached to the terminal device 100.

In addition, when an inner cover (not shown) is included in the battery cover, the control circuit 119, the communication module, and the contact point 120 may be arranged on the inner cover, whereas the battery cover may include the contact point 120 for contacting the constituent elements arranged on the inner cover and the conductive electrode 115 to 118.

A method of measuring a physiological signal at the above-described physiological signal measurement apparatus or the terminal device is described below with reference to FIGS. 7 to 9.

Figure 7:
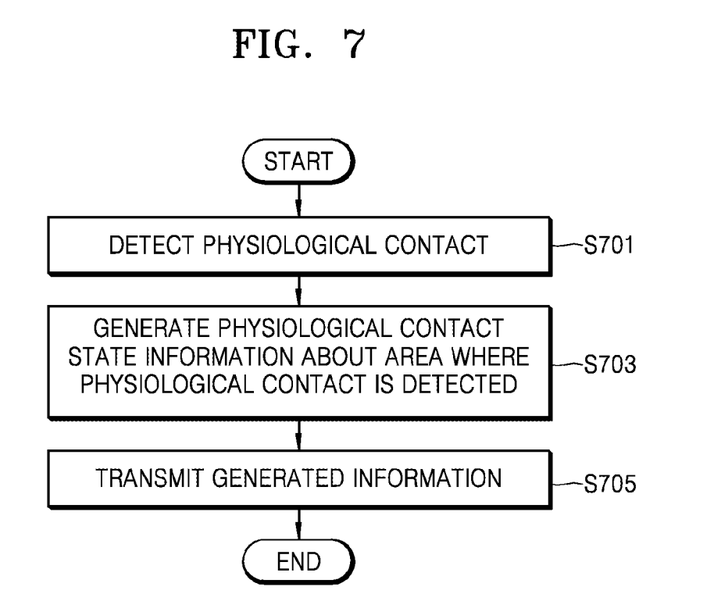
FIG. 7 is a flowchart showing a method of measuring a physiological signal according to an embodiment of the present invention.

FIG. 7 is a flowchart showing a method of measuring a physiological signal at the physiological signal measurement apparatus 200 according to an embodiment of the present invention.

Referring to FIG. 7, in Operation 701, the physiological signal measurement apparatus 200 may detect a physiological contact. The physiological signal measurement apparatus 200 may start the detection of a physiological contact upon a physiological signal measurement request that is received from the outside.

The physiological signal measurement apparatus 200 may remove noise that may be generated when the electrodes are shared during the measurement of a physiological signal, by activating only a sensor capable of measuring the physiological signal upon the physiological signal measurement request. For example, when pulse wave signals are measured, only an optical sensor for measuring a pulse wave signal is activated and the conductive electrode may be deactivated.

As the physiological contact is detected in Operation S701, the physiological signal measurement apparatus 200 may generate physiological contact state information about an area where a physiological contact is detected to determine whether the physiological signal is in a measurable state, in Operation S703. Since a physiological portion contacts the conductive electrode over a predetermined width of the conductive electrode so that the physiological signal measurement apparatus 200 measures the physiological signal, it may be first determined prior to the measurement of the physiological signal whether the physiological signal is in a measurable state.

The physiological signal measurement apparatus 200 may generate the physiological contact state information including information about the area of the physiological portion that contacts the conductive electrode, based on a result of the detection by the sensor unit 220. The physiological contact state information may further include information that is used as a standard for determining whether the physiological signal is in a measurable state, in addition to the information about the area of the physiological portion that contacts the conductive electrode.

In Operation S705, the physiological signal measurement apparatus 200 may transmit the information generated in Operation S703 to an apparatus that receives the physiological signal measurement request.

Alternatively, the physiological signal measurement apparatus 200 may determine whether the physiological signal is measurable based on the information generated in Operation S703 and transmit a result of the determination to the physiological signal measurement apparatus 200.

In addition, the physiological signal measurement apparatus 200 may measure the physiological signal based on the determination result and transmit the physiological signal or data including a result of analysis of the physiological signal to the apparatus that received the physiological signal measurement request.

The physiological signal measurement apparatus 200 according to the present embodiment may measure the physiological signal through the sensor unit 220 of the physiological signal measurement apparatus 200 until the conditions on a set time and a measured signal are met. The measured physiological signal may be transmitted to the terminal device 400 or the external device by a wired or wireless communication.

Figure 8:
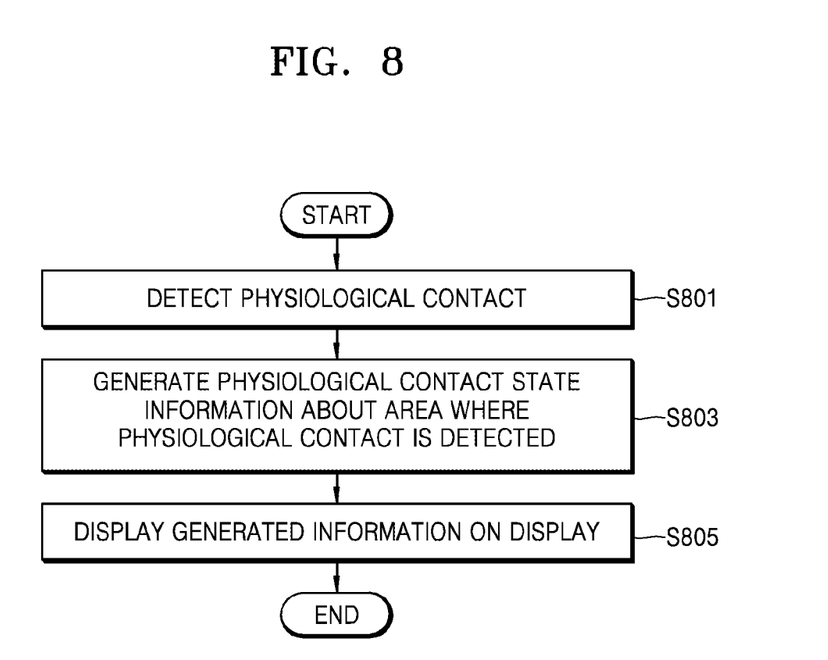
FIGS. 8 and 9 are flowcharts showing a method of measuring a physiological signal at a terminal device according to an embodiment of the present invention terminal device.
Figure 9:
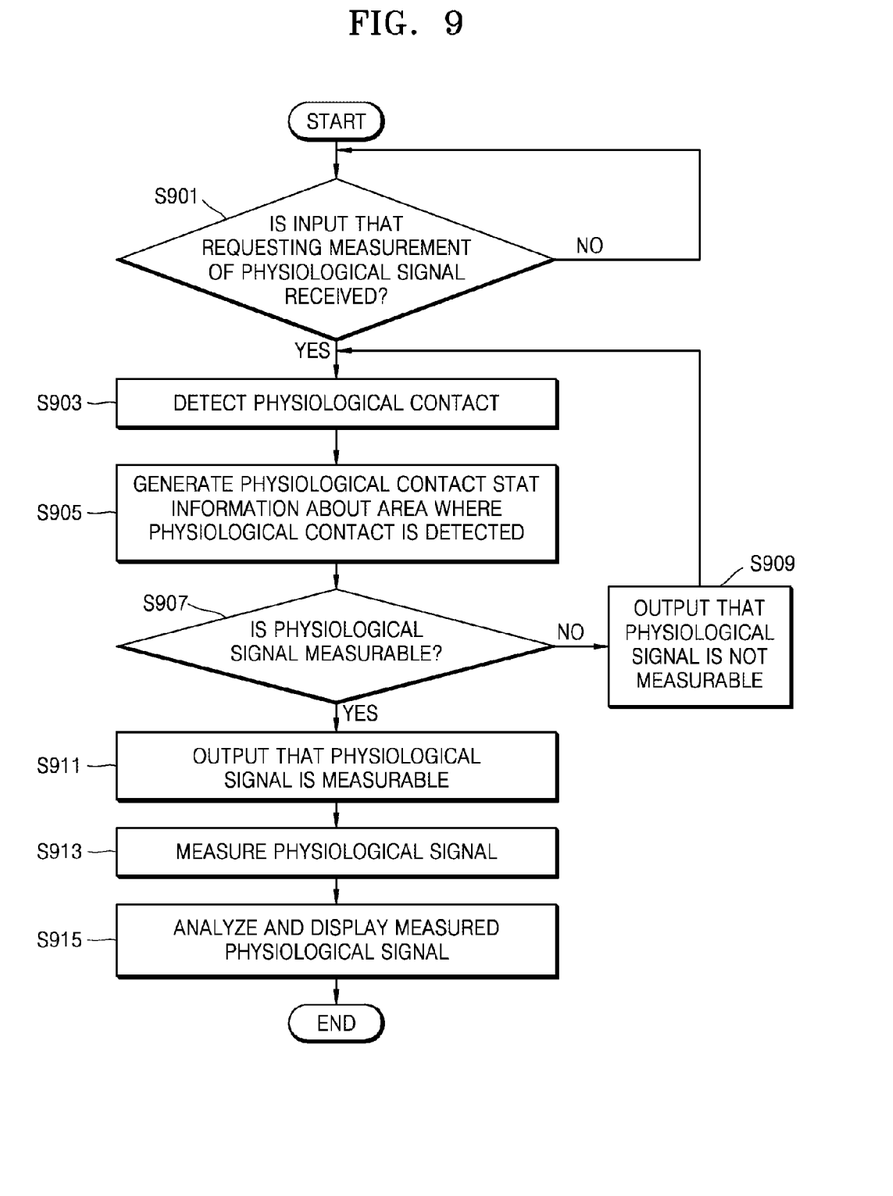

FIGS. 8 and 9 are flowcharts showing a method of measuring a physiological signal at the terminal device 400 according to an embodiment of the present invention terminal device. The terminal device 400 may include the physiological signal measurement unit 410.

A method of measuring the physiological signal at the terminal device 400 according to whether the physiological signal is measurable is described below with reference to FIG. 8.

Since Operations S801 and S803 in FIG. 8 respectively correspond to Operations S701 and S703 in FIG. 7, redundant descriptions thereof are omitted.

Referring to FIG. 8, in Operation S801, the physiological signal measurement unit 410 of the terminal device 400 may detect a physiological contact. The terminal device 400 may detect a physiological contact by requesting the physiological signal measurement unit 410 to start detection of a physiological contact according to a user input.

The terminal device 400 may perform the measurement and analysis of the physiological signal by executing an application related to the measurement of the physiological signal. When the application is executed, the terminal device 400 may activate only a sensor capable of measuring the physiological signal according to the physiological signal measurement request. When the physiological signal is measured, noise that is generated when the electrodes are shared may be removed. For example, when a pulse wave signal is measured, only an optical sensor for measuring the pulse wave signal is activated and the conductive electrode may be deactivated.

In Operation S803, as the physiological contact is detected in Operation S801, the physiological signal measurement unit 410 of the terminal device 400 may generate physiological contact state information about an area where the physiological contact is detected to determine whether the physiological signal is measurable. The physiological contact state information may further include information that is used as a standard for determining whether the physiological signal is in a measurable state, in addition to the information about the area of the physiological portion that contacts the conductive electrode.

In Operation S805, the terminal device 400 may determine whether the physiological signal is measurable based on the physiological contact state information generated by the physiological signal measurement unit 410 and display a result of the determination on the display 440 or output the result via a sound signal or vibration signal. Alternatively, the terminal device 400 may receive from the physiological signal measurement unit 410 the information about whether the measurement of the physiological signal that is determined by the physiological signal measurement unit 410 and display the information on the display 440 or output the information by sound or vibration.

A method of measuring a physiological signal at a terminal device by detecting a user input is described below with reference to FIG. 9.

Referring to FIG. 9, in Operation S901, the terminal device 400 may receive a user input requesting measurement of a physiological signal. For example, the terminal device 400 may detect a user input in a predetermined area of the display 440 that is configured to be a touch screen, in order to enable the terminal device 400 to start automatic measurement without an abnormal or unintended measurement start error occurring when a user contacts the conductive electrode by using a finger.

In Operation S903, the terminal device 400 may detect a physiological contact through the conductive electrode according to the user input received in Operation S901.

In Operation S905, as the physiological contact is detected in Operation S903, the terminal device 400 may generate physiological contact state information about the area where the physiological contact is detected so as to determine whether a physiological signal is measurable. The physiological contact state information may further include information that is used as a standard for determining whether the physiological signal is in a measurable state, in addition to the information about the area of the physiological portion that contacts the conductive electrode.

In Operation S907, the terminal device 400 may determine whether the physiological signal is currently measurable based on the physiological contact state information generated in Operation S905.

In Operation S907, when it is determined that the physiological signal is not measurable, in Operation S909, the terminal device 400 may display through the display 440 that the physiological signal is not measurable or output such information by sound or vibration.

In Operation S907, when it is determined that the physiological signal is measurable, in Operation S911, the terminal device 400 may display through the display 440 that the physiological signal is measurable or output such information by sound or vibration.

In Operation S913, the terminal device 400 may measure a physiological signal. In Operation S915, the measured physiological signal may be analyzed and a result of the analysis may be displayed. In doing so, the measurement of a physiological signal may be automatically started as an input in a predetermined area of the display 440 is detected and then a physiological contact on the sensor or conductive electrode of the physiological signal measurement unit 410 for the measurement of a physiological signal is detected. In contrast, as a physiological contact on the sensor or conductive electrode of the physiological signal measurement unit 410 for the measurement of a physiological signal is detected and then an input in a predetermined area of the display 440 is detected, the measurement of a physiological signal may be automatically started.

In addition, an acceleration sensor or a gyro sensor of the terminal device 400 may be used to remove an error that may occur as the terminal device 400 is shaken during the measurement of a physiological signal. In other words, the terminal device 400 may detect shaking of the terminal device 400 by using the acceleration sensor or the gyro sensor and a measured physiological signal passes through a filter for removing noise. Thus, the error that may occur due to the shaking of the terminal device 400 may be removed.

As described above, the operations of FIG. 9 are described to be performed within terminal device 400. However, the present invention is not limited thereto, and a predetermined physiological signal measurement apparatus connected to the terminal device 400 may detect a contact or measure a physiological signal and transmit a result thereof to the terminal device 400. The predetermined physiological signal measurement apparatus may include not only the physiological signal measurement apparatus 100 according to an embodiment of the present invention, but also the physiological signal measurement apparatus 100 having a different structure.

Figure 10:
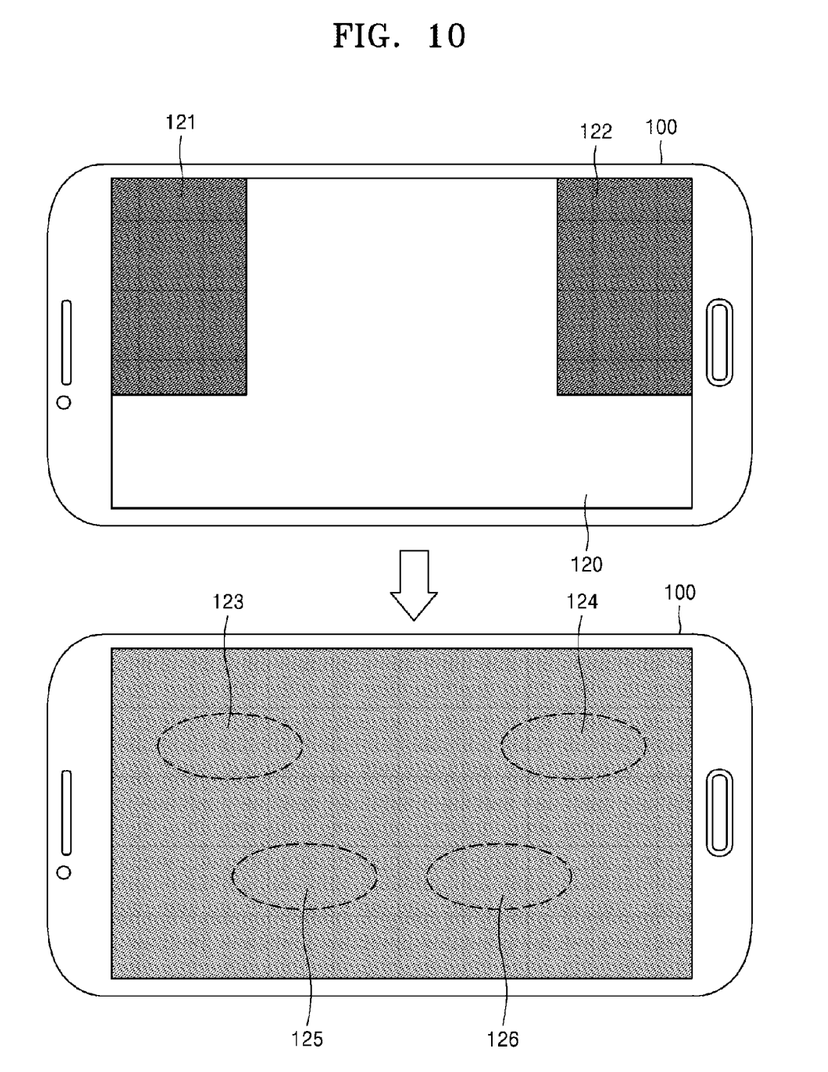
FIGS. 10 and 11 illustrate an example of a user interface for measuring a physiological signal at a terminal device according to an embodiment of the present invention terminal device.
Figure 11:
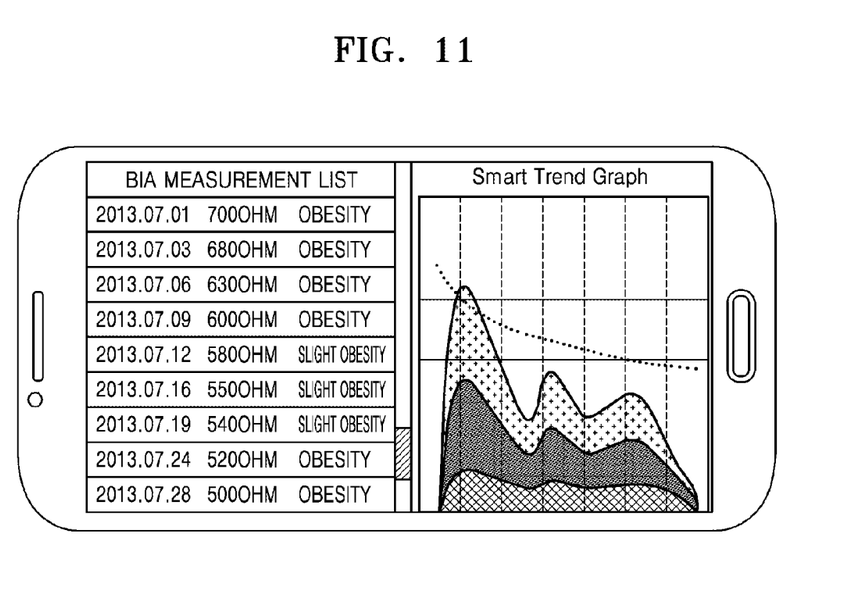

FIGS. 10 and 11 illustrate an example of a user interface for measuring a physiological signal at a terminal device according to an embodiment of the present invention terminal device.

Referring to FIG. 10, the measurement of a physiological signal may be started as a user input is detected in predetermined areas 121 and 122 of the display 120, as in Operation S901 of FIG. 9. For example, the measurement of a physiological signal may be started as two thumbs of a user are detected in the predetermined areas 121 and 122 of the display 120 and then other fingers of the user are detected in the conductive electrodes of the battery cover. Alternatively, the measurement of a physiological signal may be started as two thumbs of a user are detected in the predetermined areas 121 and 122 of the display 120 and then other fingers of the user are detected in the sensor or conductive electrodes for physiological signal measurement of the physiological signal measurement unit 410. Alternatively, the measurement of a physiological signal may be started as other fingers of the user are detected in the sensor or conductive electrodes for physiological signal measurement of the physiological signal measurement unit 410 and then two thumbs of a user are detected in the predetermined areas 121 and 122 of the display 120. Although the thumbs are described as being detected in the predetermined area of the display, the present invention is not limited thereto and the measurement of a physiological signal may be started as other physiological portion is detected. Also, the physiological signal may be measured while the two thumbs of a user are detected in the predetermined areas 121 and 122 of the display 120. When the two thumbs of a user are not detected in the predetermined areas 121 and 122, the measurement of a physiological signal may be stopped.

When measurement of a physiological signal is started as a user input requesting the measurement of a physiological signal is detected, the physiological contact state information to determine whether a physiological signal is measurable may be displayed as illustrated in a lower side of FIG. 10. For example, to easily check whether a contact of a user's finger has occurred, the terminal device 100 may display the positions of the conductive electrodes in display areas 123 to 126 that perpendicularly match the positions of the conductive electrodes on the battery cover. When a finger contacts the conductive electrode, the terminal device 100 may display a contacted area on the display. When it is determined that a physiological signal is measurable, such information may be displayed on the display or output by sound or vibration.

In addition, although the physiological signal measurement unit 410 or the physiological signal measurement apparatus 200 may measure the physiological signal through a finger contact as described above, a physiological signal may be measured through a chest skin contact as the sensor unit 220 contacts the chest skin of a human through a chest belt.

Referring to FIG. 11, a result of the measurement of a physiological signal may be displayed on the display of the terminal device 100 via a graph and a plurality of values. The measurement result may be displayed vertically or horizontally in a direction along the terminal device 100. Also, a changing direction may be checked by displaying an accumulated change in the measured physiological signal.

According to another embodiment of the present invention, an apparatus for measuring a physiological signal is included in the battery cover of a mobile terminal, and thus, a size or thickness of the mobile terminal may not be increased.

According to another embodiment of the present invention, the physiological signal may be measured by using power of a mobile terminal.

The invention can also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, optical data storage devices, etc. The computer readable recording medium can also be distributed over network coupled computer systems so that the computer readable code is stored and executed in a distributed fashion.

While this invention has been particularly shown and described with reference to preferred embodiments thereof, it will be understood by those of ordinary skill in the art that various changes in form and details may be made therein without departing from the spirit and scope of the invention as defined by the appended claims. The preferred embodiments should be considered in descriptive sense only and not for purposes of limitation. Therefore, the scope of the invention is defined not by the detailed description of the invention but by the appended claims, and all differences within the scope will be construed as being included in the present invention.

The invention claimed is:

1. An electronic device comprising:
   a sensor;
   a display; and
   a processor configured to:
      control the sensor to receive a first user input for displaying a user interface for receiving a second user input;
      control the display to display the user interface for receiving the second user input, in response to the first user input being received by the sensor; and
      in response to the second user input being received through the user interface displayed on the display, control the sensor to sense biological information of a user holding the electronic device while the first user input and the second user input are received in the electronic device.

2. The electronic device of claim 1, wherein the sensor is disposed in an opposite side of the electronic device with respect to the display.

3. The electronic device of claim 1, wherein the display is a touch screen.

4. The electronic device of claim 1, wherein the processor is further configured to control the sensor to:
   generate first information related to an area where the biological information of the user is sensed; and
   determine whether the sensor is able to sense the biological information of the user, based on the first information that is generated.

5. The electronic device of claim 4, wherein the processor is further configured to control the display to display either one or both of the first information related to the area where the biological information of the user is sensed and second information related to a condition that the sensor is able to sense the biological information of the user.

6. The electronic device of claim 1, wherein the processor is further configured to control the display to display the biological information of the user that is sensed by the sensor.

7. The electronic device of claim 2, wherein the processor is further configured to control the display to display, on the user interface, a display area that perpendicularly matches a position of the sensor in the opposite side of the electronic device with respect to the display, in response to the first user input being received by the sensor.

8. An electronic device comprising:
a sensor;
a display; and
a processor configured to:
   control the sensor to receive a first user input for sensing a biological signal of a user holding the electronic device;
   sense the biological signal of the user holding the electronic device, in response to the first user input being received by the sensor;
   generate first information related to an area where the biological signal of the user is sensed by the sensor, in response to the first user input being received by the sensor;
   determine whether the sensor is able to measure biological information of the user by sensing the biological signal, based on the first information and second information; and
   control the sensor to measure the biological information of the user holding the electronic device by sensing the biological signal, based on the determination.

9. A method of sensing biological information of a user holding an electronic device, the method being performed by the electronic device and comprising:
   receiving, by a sensor, a first user input for displaying a user interface for receiving a second user input;
   in response to the first user input being received by the sensor, displaying, in predetermined areas of a display, the user interface for receiving the second user input for sensing biological information of the user holding the electronic device;
   receiving, through the user interface, the second user input for sensing the biological information of the user holding the electronic device; and
   in response to the second user input being received through the user interface displayed on the display, sensing, by the sensor, the biological information of the user holding the electronic device while the first user input and the second user input are received in the electronic device.

10. The method of claim 9, wherein the sensor is disposed in an opposite side of the electronic device with respect to the display.

11. The method of claim 9, wherein the display is a touch screen.

12. The method of claim 9, further comprising:
generating first information related to an area in the sensor where the biological information of the user is sensed; and
determining whether the sensor is able to sense the biological information of the user, based on the first information that is generated.

13. The method of claim 12, further comprising:
displaying either one or both of the first information related to the area where the biological information of the user is sensed and second information related to a condition that the sensor is able to sense the biological information of the user.

14. The method of claim 9, further comprising:
displaying the biological information of the user that is sensed by the sensor.

\* \* \* \* \*